(12) United States Patent
Ooyauchi

(10) Patent No.: US 6,843,783 B2
(45) Date of Patent: Jan. 18, 2005

(54) INJECTION NEEDLE AND INJECTION APPARATUS

(75) Inventor: Tetsuya Ooyauchi, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/772,910

(22) Filed: Jan. 31, 2001

(65) Prior Publication Data

US 2002/0052580 A1 May 2, 2002

(30) Foreign Application Priority Data

Sep. 14, 2000 (JP) .............................. 2000-280361
Dec. 21, 2000 (JP) .............................. 2000-389248

(51) Int. Cl.⁷ .......................... A61M 5/00; A61M 5/24; A61M 5/32
(52) U.S. Cl. .................. 604/239; 604/201; 604/272
(58) Field of Search ........................ 604/239, 264, 604/272, 200–204, 206, 273, 274, 412, 413

(56) References Cited

U.S. PATENT DOCUMENTS

| | | | |
|---|---|---|---|
| 1,746,009 A | | 2/1930 | Mulford |
| 2,187,259 A | | 1/1940 | Barnhart |
| 2,830,587 A | * | 4/1958 | Everett .................... 604/272 |
| 3,123,073 A | | 3/1964 | Barr, Sr. et al. |
| 3,344,787 A | | 10/1967 | Maclean |
| 3,884,229 A | | 5/1975 | Raines et al. |
| 3,974,832 A | | 8/1976 | Kruck |
| 4,266,543 A | | 5/1981 | Blum |
| 4,944,677 A | * | 7/1990 | Alexandre .................. 433/134 |
| 5,383,930 A | * | 1/1995 | Brannan et al. ............ 128/898 |
| 5,688,246 A | * | 11/1997 | Waitz et al. ............ 604/164.11 |
| 5,792,099 A | * | 8/1998 | DeCamp et al. ............ 604/506 |
| 5,951,528 A | | 9/1999 | Parkin |
| 5,984,906 A | | 11/1999 | Bonnichsen et al. |
| 6,146,361 A | * | 11/2000 | DiBiasi et al. .............. 604/232 |

FOREIGN PATENT DOCUMENTS

| | | |
|---|---|---|
| EP | 0 047 398 | 12/1984 |
| EP | 0 895 481 | 9/2000 |
| JP | 8-10327 | 1/1996 |

* cited by examiner

*Primary Examiner*—Michael J. Hayes
(74) *Attorney, Agent, or Firm*—Burns, Doane, Swecker & Mathis, L.L.P.

(57) ABSTRACT

A drug injection needle comprises a puncturing needle part having a puncturing part capable of puncturing a body, a drug introducing needle part capable of communicating with the inside of the drug container, and a housing supporting the puncturing needle part and the drug introducing needle part to allow the liquid drug to flow between the needle parts. The outer diameter of the puncturing part is not more than 0.254 mm. The outer diameter of the drug introducing needle part is larger than at least that of the vicinity of the distal end of the puncturing part of the puncturing needle part, and a cutting edge is formed at the end of the drug introducing needle part for penetrating through an elastic member that is provided to seal the drug injection port of the drug container.

6 Claims, 11 Drawing Sheets

INJECTION NEEDLE AND INJECTION APPARATUS

BACKGROUND OF THE INVENTION

1. Field of the Invention

The invention relates to an injection needle and an injection apparatus, more specifically to an injection needle and an injection apparatus used for injecting liquid drugs into a body.

2. Description of the Related Art

FIG. 1 and FIG. 2 show a typical injection needle used for injecting liquid drugs into a living body, particularly intradermal, subcutaneous, and muscle tissue layers.

As shown in these drawings, a drug injection needle 101 consists of a needle 102 and a base 104 that supports the needle 102. The needle 102 consists of a hollow needle of a constant outer diameter and is affixed to the base 104. A cutting edge 131 is formed at the proximate end of the needle 102. Furthermore, a female screw 143 is formed on the internal surface of the base 104.

The drug injection needle 101 is typically attached to the drug injection port formed on the nose of a drug container (not shown) containing a liquid drug. A male screw is formed on the drug injection port of the drug container, and the drug injection needle 101 is attached to the drug container when the female screw 143 of the drug injection needle 101 is screwed onto this male screw of the drug container.

The drug injection port of the drug container is sealed by a rubber stopper (not shown). The inside of the needle 102 communicates with the inside of the drug container when a cutting edge 131, which is formed on the proximate side of the needle 102, penetrates said rubber stopper as the drug injection needle 101 is attached to the drug container.

However, the needle 102 of the conventional drug injection needle 101 typically has a relatively large diameter of 0.25 mm or larger. Therefore, it causes a pain when the needle 102 punctures a living body or when a liquid drug is injected into a living body. The thought of puncturing with such a thick needle also causes fear or threat to patients.

Another problem is that it is extremely difficult to assemble a thin needle firmly to the base in the middle of the needle as shown in FIG. 2, if it is attempted to use a thinner needle in order to reduce the pains of patients.

Furthermore, such a thin needle tends to be too weak. Therefore, the needle may not be able to penetrate through the rubber stopper provided on the drug injection port of the drug container and may end up breaking when it is attempted to install the needle on the drug container.

Moreover, such a thin needle inherently has a thin inner diameter so that its liquid path resistance during injection ("injection resistance"), aggravated by its relatively long length, becomes extremely large. Thus, it has a problem that it requires a substantially large force to push out the liquid drug during injection.

More specifically, in case of the drug injection needle used by diabetes patients for intravenous self-injection of insulin solutions, even the thinnest one available on the market has an outer diameter of 0.254 mm (31 gage (G)). The "gage" is a number based on the B.W.G. (Birmingham Wire Gage).

When this needle with an outer diameter of 0.254 mm (31 G) is used, the injection resistance becomes fairly high as a result of the fact that the injection resistance of the needle increases in inverse proportion with the fourth power of the diameter of the needle. This makes it difficult for a person, who is a physically or mentally weak patient and doesn't have a sufficient force to push the plunger of the drug injection apparatus, such as a woman, child or an aged person, to inject liquid drugs subcutaneously using needles with an outer diameter of 0.254 mm (31 G). In such a case, the patient has to use thicker needles such as the one with an outer diameter of 0.30 mm (30 G).

When a needle with a 0.254 mm (31 G) outer diameter is used, the insulin solution sometimes overflows from the punctured opening of the skin or the tip of the needle. One of the reasons why it happens is suspected to be that the patient tends to pull out the needle prematurely without waiting for a specified amount of the liquid drug (specified insulin unit) to be completely administered subcutaneously because it takes too long for the liquid drug to be completely injected because of the high liquid path resistance of such a thin needle with an outer diameter of 0.254 mm (31 G). For a diabetes patient, it is important to accurately administer the specified amount of the liquid drug, which is determined by the doctor. Overflowing of the liquid drug after injection means that less than the specified amount of the liquid drug is administered and that the treatment is not sufficiently performed.

An example in another field is a dental drug injection apparatus used to inject a liquid anesthetic agent (lidocaine) into dental pulp. The outer diameter of the thinnest needle (dental needle) for the dental drug injection apparatus available on the market is 0.26 mm. There is also a substantially high injection resistance in injecting the anesthetic agent into dental pulp, etc., using a needle with an outer diameter of 0.26 mm. The main body and the plunger of the dental drug injection apparatus are made of metal and a doctor who is a healthy person operates them. Therefore, it is possible to inject the liquid anesthetic agent even with such a thin needle as the doctor can push the plunger very hard.

However, it is preferable to be able to inject with a smaller force and also to use a thinner needle in such a dental drug injection apparatus in order to reduce the pain it gives to the patient. A metallic injection apparatus is heavy. It will be able to provide a lighter and easier to handle dental drug injection apparatus if the injection resistance of the needle can be reduced so that a lighter material such as plastic can be used.

As can be seen from the above, it has been impossible to reduce the outer diameter of the needle to alleviate the patient's pain because of those problems mentioned above.

SUMMARY OF THE INVENTION

The object of this invention is to provide an injection needle and an injection apparatus that are capable of reducing patients' pains, can be manufactured easily, and have a sufficient strength to penetrate rubber stoppers and a less injection resistance.

The specific object of the invention is to provide an injection needle to be attached to a liquid injection port formed on the distal end of a liquid container that contains a liquid inside, comprising:

a puncturing needle part that has a puncturing part that is capable of puncturing a body;

a liquid introducing needle part that is capable of communicating with the inside of said liquid container; and a base that supports said puncturing needle part and said liquid introducing needle part in such a way as to allow the liquid to flow between the two needle parts, wherein;

said puncturing part has an outer diameter which is not more than 0.254 mm, said liquid introducing needle part has a larger outer diameter than at least the vicinity of the distal end of said puncturing part; and a cutting edge is formed at the end of said liquid introducing needle part for penetrating through an elastic member that is provided to seal the liquid injection port.

According to the injection needle of this invention, it is possible to make the puncture part of the needle that is capable of puncturing a body thinner than it used to be. Consequently, it is possible to reduce the area of the needle that contacts with the nerve net, minimize the attack on the nerve net, and alleviate the patient's pain.

Furthermore, the injection needle of this invention is not intended to affix the needle with a thin, constant diameter needle to the base at the middle of its length. Therefore, it is easy to assemble and manufacture the injection needle even though the puncturing part of the needle is thin.

As the cutting edge can be formed at the end of the liquid introducing needle part, which has a relatively thicker diameter, for penetrating the elastic member that is used to seal the liquid injection port of the liquid container, it can have a sufficient strength to penetrate through the elastic member. Consequently, it is possible to prevent a situation where the needle breaks and cannot penetrate though the elastic member.

Moreover, by thickening the liquid introducing needle part, the injection resistance can be reduced. Therefore, the force required for injecting the liquid drug can be reduced and the liquid drug can be injected into the body more ideally.

Consequently, the invention provides a thinner injection needle that causes no pain or extremely small pains and yet causes less injection resistance by making the part that punctures the patient's skin thinner and other parts of the needle relatively thicker. In particular, by setting the outer diameter of the puncturing part to be not more than 0.254 mm, or preferably in the range of 0.1–0.25 mm, or more preferably in the range of 0.18–0.22 mm, it is possible to have a puncturing part equal or thinner than the thinnest needle currently available on the market, and yet reduce the injection resistance simultaneously. Therefore, it is possible to provide an injection needle that is capable of administering liquid drugs quickly and easily even when it is operated by a patient who is physically or mentally weak such as a woman, child and an aged person.

Another specific object of the invention is to provide an injection apparatus including a liquid container that contains liquid inside and has a liquid injection port formed on its distal end and an elastic member provided to seal the liquid injection port, and an injection needle that is attached to the liquid injection port of said liquid container, wherein:

said injection needle comprises a puncturing needle part that has a puncturing part that is capable of puncturing a body, a liquid introducing needle part that is capable of communicating with the inside of said liquid container, and a base that supports said puncturing needle part and said liquid introducing needle part in such a way as to allow the liquid flow between the two needle parts;

said puncturing part has an outer diameter which is not more than 0.254 mm, said liquid introducing needle part has a larger outer diameter than at least the distal end of said puncturing part; and a cutting edge is formed at the end of said liquid introducing needle part for penetrating through said elastic member.

The objects, features and characteristics of this invention other than those set forth above will become apparent from the description given herein below with reference to preferred embodiments illustrated in the accompanying drawings.

DETAILED DESCRIPTION OF THE PREFERRED EMBODIMENT

The embodiments of this invention will be described below with reference to the accompanying drawings.

Figure 1:
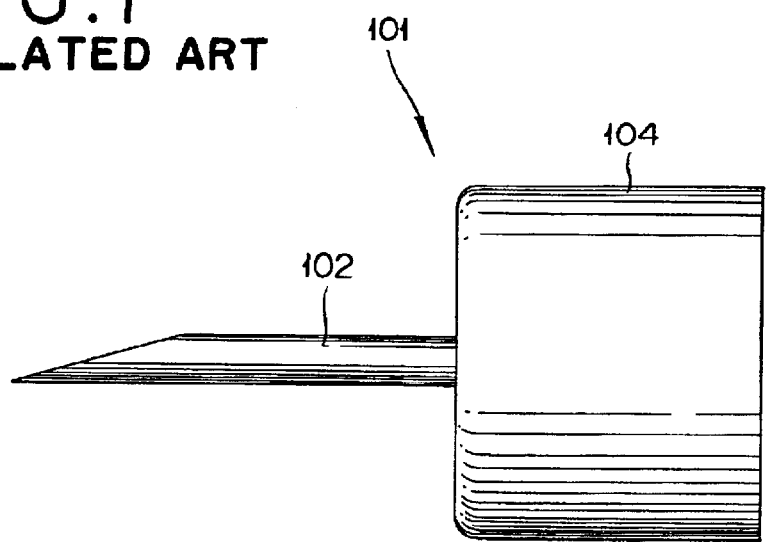
FIG. 1 is a side view of a conventional drug injection needle.
Figure 2:
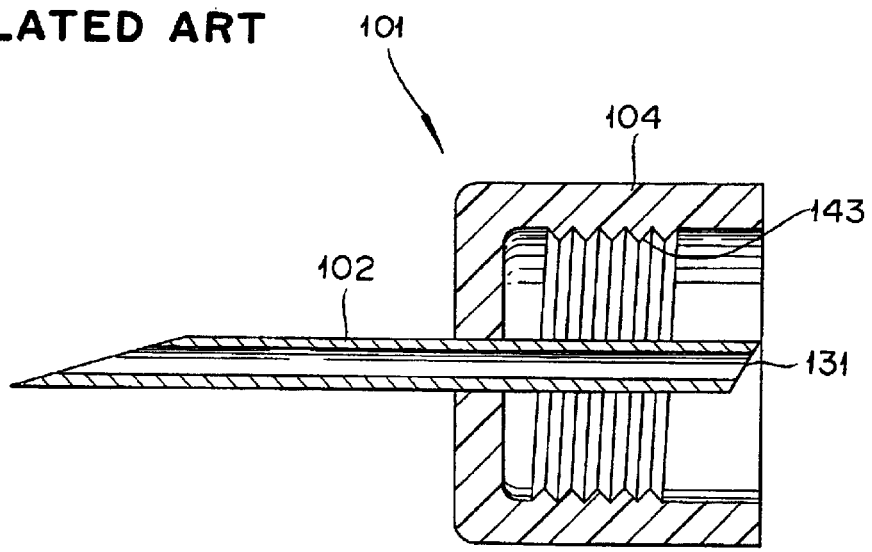
FIG. 2 is a cross sectional view of a conventional drug injection needle.
Figure 3:
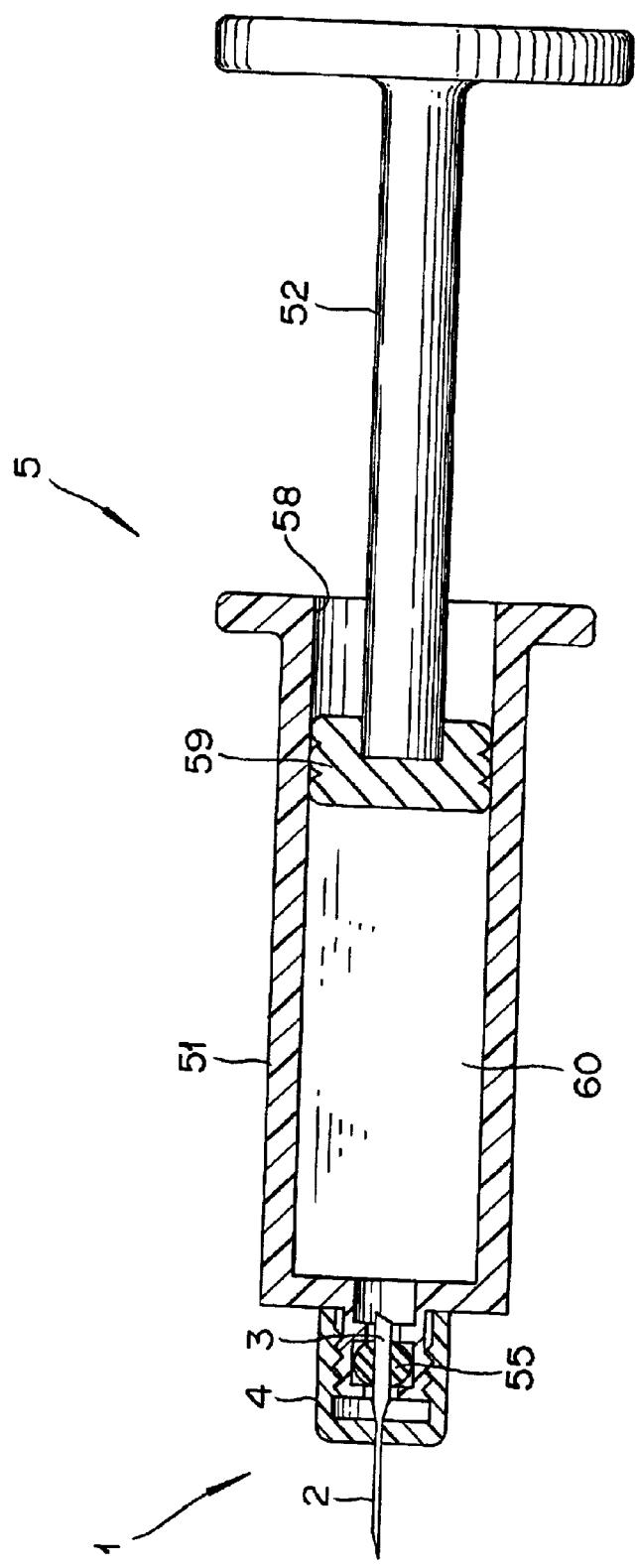
FIG. 3 is a cross sectional view of a drug injection apparatus equipped with a drug injection needle according to a first embodiment of the invention.
Figure 4:
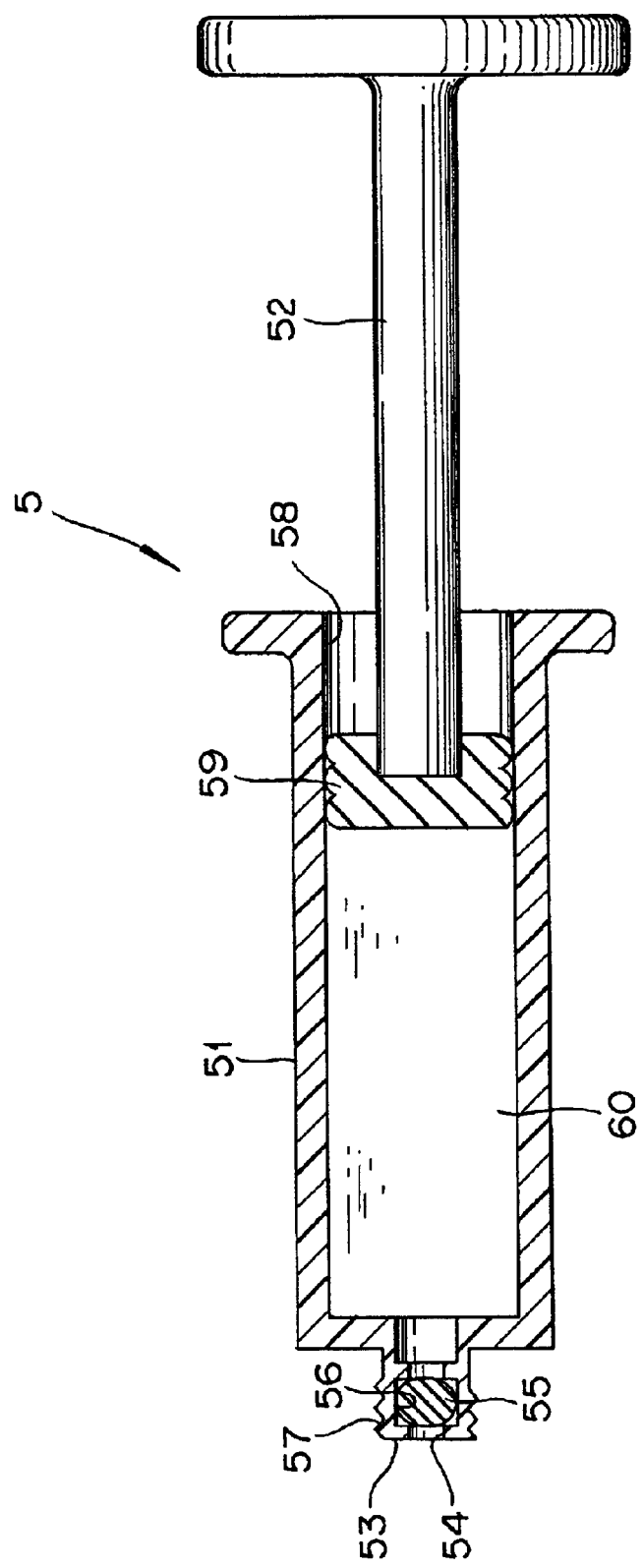
FIG. 4 is a cross sectional view of a drug injector main body show in FIG. 3.
Figure 5:
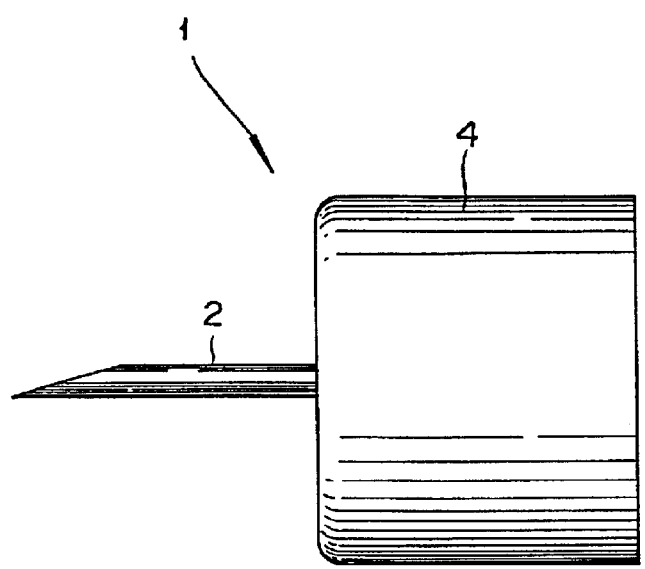
FIG. 5 is a side view of the drug injection needle show in FIG. 3.
Figure 6:
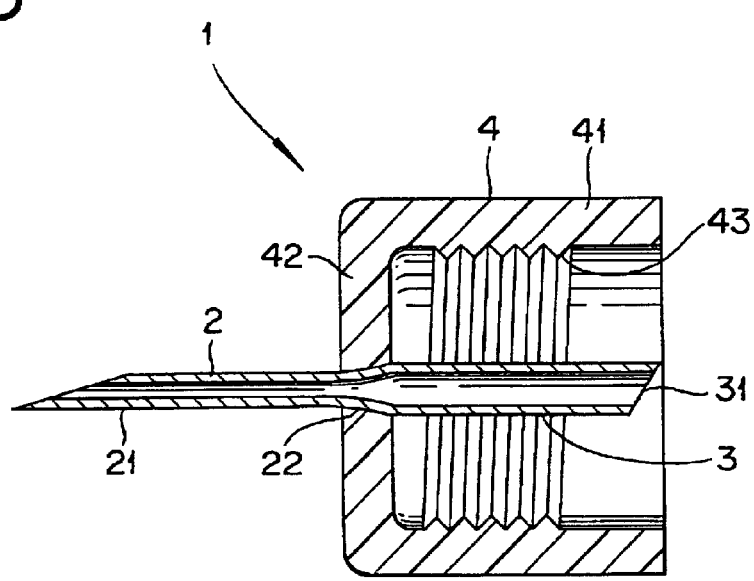
FIG. 6 is a cross sectional view of the drug injection needle show in FIG. 3.

FIG. 3 is a cross sectional view of a drug injection apparatus equipped with a drug injection needle according to a first embodiment of the invention; FIG. 4 is a cross sectional view of a drug injector main body show in FIG. 3; FIG. 5 is a side view of the drug injection needle show in FIG. 3; and FIG. 6 is a cross sectional view of the drug injection needle show in FIG. 3.

The drug injection apparatus shown in FIG. 3 includes a drug injection needle 1 and an injector main body 5, and injects liquid drug 60 through the distal end of the drug injection needle 1 when a plunger 52 is pushed.

As shown in FIG. 4, the injector main body 5 comprises a drug container 51, which is of a substantially cylindrical shape and holds the liquid drug 60 inside, and the plunger 52 that is capable of moving reciprocally and axially inside the drug container 51.

A drug injection port 54 is formed on a boss 53 provided on the distal end (left hand side in the drawing) of the drug container 51, this drug injection port 54 is sealed by an elastic member 55 such as a rubber stopper. The elastic member 55 is held in place by being fitted into a groove 56 formed inside of the boss 53. A male screw 57 is formed on the outside of the boss 53 to be used for attaching the drug injection needle 1.

On the other hand, an opening 58 is formed on the proximate end (right hand side in the drawing) of the drug container 51. The plunger 52 is inserted through the opening 58. A gasket 59 is attached to the distal end of the plunger 52. The purpose of the gasket 59 is to seal by fitting closely with the inner surface of the drug container 51 to prevent the liquid drug 60 from leaking backward, and to push the liquid drug forward by moving toward the distal side.

The space between the elastic member 55 and the gasket 59 is filled with the liquid drug 60. The liquid drug 60 used in this drug injection apparatus can be either a solution, gel or suspension fluid containing a drug. Any drug can be used as long as it is suitable for percutaneous administration. The drug can be the one that is applicable locally or for the entire body.

The elastic member 55 and the gasket 59 are made by forming such materials as butyl rubber, silicone rubber, elastomer, etc. The drug liquid container 51 and the plunger 52 are formed by molding plastics such as polypropylene and polyethylene or glass. The drug container 51 is totally or partially made of a clear material and its contents can be observed visually.

As shown in FIG. 5 and FIG. 6, the drug injection needle 1 comprises a puncturing needle part 2 that has a puncturing part 21 that is capable of puncturing a living body, a liquid introducing needle part 3 that is capable of communicating with the inside of the drug container 51, and a housing 4, which is a base that supports the puncturing needle part 2 and the drug introducing needle part 3 in such a way as to allow the liquid drug to flow between the needle parts 2 and 3. In the first embodiment, the puncturing needle part 2 and the drug introducing needle part 3 constitute a single needle body.

The housing 4 comprises a cylindrical part 41 and a bottom wall 42 formed on one end of the cylindrical part 41. A female screw 43 is formed on the inner surface of the cylindrical part 41 to engage with the male screw 57 formed on the boss 53 of the drug container 51.

The puncturing needle part 2 and the drug introducing needle part 3 constitute a hollow needle. The puncturing needle part 2 is formed on the distal side of the drug injection needle 1 and the drug introducing needle part 3 is formed on the proximate side of the puncturing needle part 2. The drug introducing needle part 3 has a larger outer diameter than that of the puncturing part 21 of the puncturing needle part 2.

The outer diameter of puncturing part 21 of the puncturing needle 2 in this embodiment is set to be not more than 0.254 mm (31 G), or preferably in the range of 0.1–0.25 mm, or more preferably in the range of 0.18–0.22 mm. As can be seen from the above, the upper limit of the outer diameter of the puncture part 21 is set to equal or less than that of the conventional 31 G needle from the standpoint of reducing the puncture pain it gives to patients, and the lower limit is set from the standpoint of securing the specified strength and suppressing the increase of the injection resistance. Accordingly, the inner diameter of the puncturing part 21 should be preferably in the range of 0.05–0.15 mm. Even if the outer diameter of the puncturing part 21 is formed 0.254 mm (31 G), same as in the conventional needle, it is still possible to provide a better needle from the standpoint of reducing the injection resistance because the outer diameter of the drug introducing part 3 is larger.

The length of the puncturing part 21 of the puncturing needle part 2 is preferably in the range of 0.2–15 mm, or more preferably in the range of 0.5–10 mm. The length of the puncturing part 21 corresponds to the length of the puncturing needle part 2 that is extending outside from the bottom wall 42 of the housing 4. The length of the puncturing part 21 has hitherto been normally 10–40 mm. On the contrary, the upper limit of the length of the puncturing part 21 in this embodiment is set shorter than that of the prior art from the standpoint of reducing the injection resistance, and its lower limit is set from the standpoint of performing the puncture a living body properly.

Figure 7:
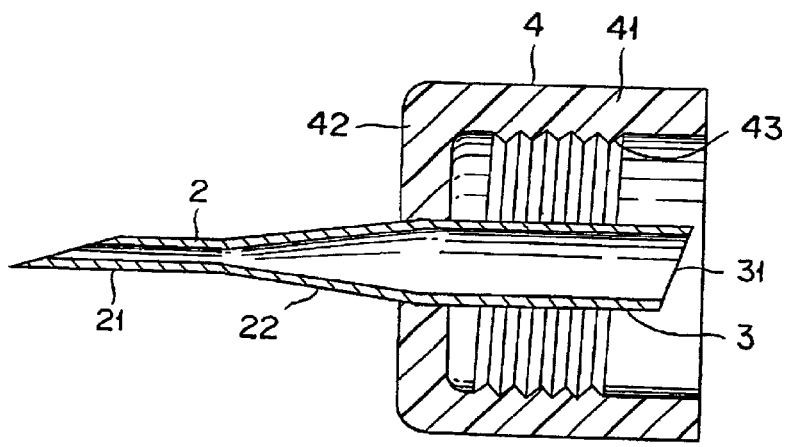
FIG. 7 is a cross sectional view of a variation of the drug injection needle according to the first embodiment of the invention.

As shown in FIG. 6 or FIG. 7, at least a portion of the puncturing part 21 has a constant outer diameter, the length of the portion is preferably as follows.

The numerical values in parentheses as listed below indicate more preferable range.

| outer diameter | length |
| --- | --- |
| 0.22–0.254 mm | 0.2–15 mm |
| | (1–15 mm) |
| 0.15–0.22 mm | 0.2–8 mm |
| | (1–8 mm) |
| 0.1–0.15 mm | 0.2–3 mm |
| | (1–3 mm) |

On the other hand, the outer diameter of the drug introducing needle part 3 is preferably in the range of 0.3–0.6 mm, or more preferably in the range of 0.35–0.5 mm. Thus, the lower limit of the outer diameter of the drug introducing needle part 3 is set larger than that of the puncturing needle part 2 as mentioned above from the standpoint of improving the strength of the part where the cutting edge 31 is formed and suppressing the increase of the injection resistance, and its upper limit is set so that the cutting edge 31 is able to penetrate easily through the elastic member 55 that seals the drug injection port 54 and also from the standpoint of easiness of manufacture. Accordingly, the inner diameter of the drug introducing needle part 3 should be preferably in the range of 0.25–0.5 mm.

The cutting edge 31 is formed on the proximate end of the drug introducing needle part 3 in order to penetrate through the elastic member 55 that seals the drug injection port 54 formed on the distal end of the drug container 51. The cutting edge 31 is, for example, formed by slicing the end of the drug introducing needle part 3 in an angle. The cutting edge 31 penetrates through the elastic member 55 when the drug injection needle 1 is attached to the drug container 51.

The puncturing needle part 2 has an intermediate part 22 that is formed between the puncturing part 21 and the drug introducing needle part 3 and connects them smoothly by changing its diameter continuously. If the drug injection needle 1 is a short needle normally used for intradermal and subcutaneous administration, the intermediate part 22 is affixed to the middle of the bottom wall 42 of the housing 4 being inserted into it.

Figure 8:
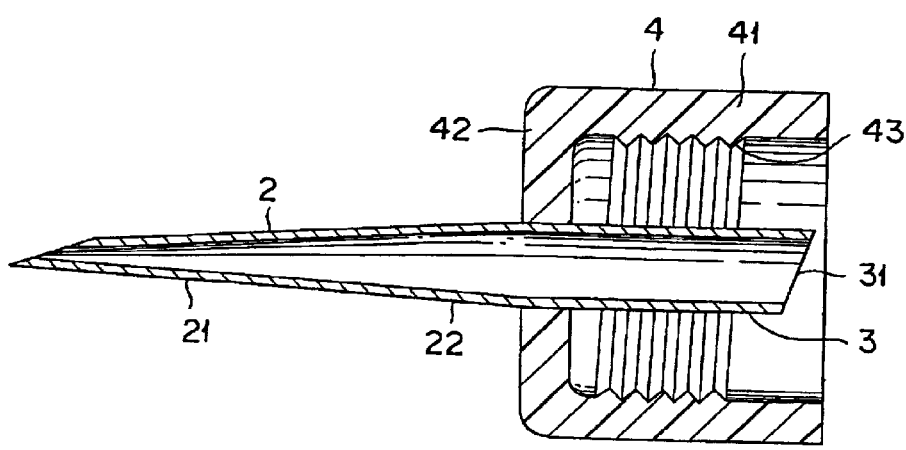
FIG. 8 is a cross sectional view of another variation of the drug injection needle according to the first embodiment of the invention.

If the drug injection needle 1 is a long needle normally used for subcutaneous and intramascular administration, it is not necessary to make the entire portion that can puncture a living body thinner than the drug introducing needle part 3. For example, it is also possible to configure in such a way as to make the intermediate part 22 with a continuously changing outer diameter to be able to puncture a living body as shown in FIG. 8, so that the intermediate part 22 is included in the puncturing part 21. In this case, the part, which is on the proximate side of the intermediate part 22 and has a constant and thick diameter, is affixed in the center of the bottom wall 42 of the housing 4 in an inserted condition.

Figure 9:
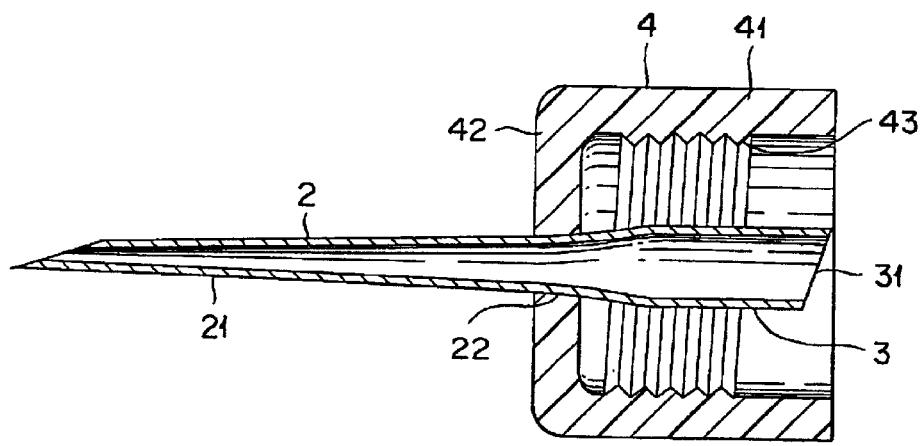
FIG. 9 is a cross sectional view of yet another variation of the drug injection needle according to the first embodiment of the invention.

Furthermore, the shape extending from the puncturing part 21 to the part, which is affixed to the bottom wall 42 of the housing 4, in this invention should not necessarily be limited to a shape having a constant outer diameter as shown in FIG. 6, but rather it can be a shape having a continuously changing outer diameter as shown in FIG. 9.

The intermediate part 22 has a shape tapering thinner toward the distal end, and the external shape line of the cross section cut by a plane including the axis is either a straight line or a concave line. The shapes of the intermediate part 22, particularly those that are shown in FIGS. 6-9, are such that the inner diameter gradually reduces toward its distal end (taper shape). Consequently, the drug liquid is accelerated and flows vigorously as it flows from the drug introducing part 3 to the puncturing part 21 via the intermediate part 22.

As shown in FIG. 8 and FIG. 9, an outer diameter of the intermediate part 22 continuously varies. However, at least a portion of the puncturing part 21 or the intermediate part 22 may have an outer diameter which stepwise vary.

When the puncturing part 21 has a portion, an outer diameter of which continuously (or stepwise) reduces toward its distal end as shown in FIG. 8 and FIG. 9, the length of the puncturing part 21 can be longer than the puncturing part 21 as shown in FIG. 6, which has a portion, an outer diameter of which is constant.

The housing 4 is formed by molding plastics such as polypropylene and polyethylene or glass. The puncturing needle part 2 and the drug introducing needle part 3 are normally produced by forming stainless steel. It is also possible to make the needle parts 2 and 3 from other metallic materials such as titanium or plastics.

The affixing of the puncturing needle part 2 and the drug introducing needle part 3 to the housing 4 is conducted by insert molding or gluing, for example, in a shape as shown in FIG. 6. Since the jointing force reduces if the needle parts 2 and 3 are uniformly thinner, the needle parts 2 and 3 may slip off toward the distal end from the housing 4. Since the needle parts 2 and 3 are jointed with the housing 4 at the intermediate part or at the part where the outer diameter is thicker in this embodiment, there is little concern that the needles 2 and 3 slip off toward the distal end. Moreover, since the jointing surface between the housing 4 and the needle parts 2 and 3 is larger, the needle parts 2 and 3 can be affixed more rigidly to the housing 4. Thus, although the puncturing part 21 of the puncturing needle art 2 is thinner, the drug injection needle 1 can be easily manufactured.

Next, let us describe the method of attaching the drug injection needle to the drug container and using the drug injection apparatus.

First, mount the housing 4 of the drug injection needle 1 on the boss 53 of the drug container 51 and let the cutting edge 31 formed on the proximate end of the drug introducing needle part 3 penetrate into the elastic member 55. This causes the inside of the needle parts 2 and 3 communicate with the inside of the drug container 51. Next, let the female screw 43 formed on the inner surface of the housing 4 of the drug injection needle 1 engage with the male screw 57 formed on the boss 53 of the drug container 51 to screw the drug injection needle 1 into the drug container 51.

Since the outer diameter of the drug introducing needle part 3 is set to be larger than that of the puncturing part 21 of the puncturing needle part 2, it is possible to secure a sufficient strength required for penetrating the elastic member 55. Thus it is possible to prevent the drug introducing needle part 3 from breaking and being unable to penetrate through the elastic member 55.

Thus the drug injection needle 1 is attached to the drug container 51, completing the preparation for the usage of the drug injection apparatus. Next, puncture the body of the patient, into which the liquid drug is to be injected, with the drug injection needle 1 of the drug injection apparatus. Since the puncturing part 21 of the puncturing needle part 2 is thinner than that of the conventional needle, the contact surface of the needle part with the nerve plexus that relates with the pain is smaller, so that the attack on the nerve plexus becomes smaller and the patient feels less pain.

By pressing the plunger 52 of the injector main body 5, the liquid drug 60 inside the drug container 51 passes through the needle parts 2 and 3 of the drug injection needle 1, and is injected into the target living body, such as intradermal, subcutaneous, or muscular tissue or various intestine, etc.

Since the outer diameter of the drug introducing needle part 3 is set relatively large, the inner diameter of the drug introducing needle part 3 can also be set larger, thus contributing to the reduction of the injection resistance. Therefore, the force required to press the plunger 52 can be smaller and the drug liquid can be injected into the living body smoothly.

Thus, the embodiment is capable of providing a drug injection needle with little injection resistance while being a drug injection needle that causes no pain at all or an extremely small pain by making the part that punctures the skin of the patient thin and other parts relatively thicker. In particular, selecting the outer diameter of the puncturing part 21 to be not more than 0.254 mm (31 G), preferably in the range of 0.1–0.25 mm, or more preferably in the range of 0.18–0.22 mm, it is possible to reduce the injection resistance while having a puncturing part that is equal or thinner than the thinnest needle available on the market. Thus, it is possible to provide a drug injection needle and the drug injection apparatus that is painless or gives extremely small pain and is capable of injecting liquid drug effortless and quickly even when it is used with a physically or mentally weak patient such as a woman, child or an aged person.

Although each of the drug injection needles shown in FIG. 5 through FIG. 9 has needle parts 2 and 3, which constitute a single needle, the drug injection needle of the invention can have multiple needle bodies on one housing 4. This will increase the amount of drug liquid injected. Also, since the drug liquid is injected in multiple streams, a quicker effect of the drug can be expected.

Figure 10:
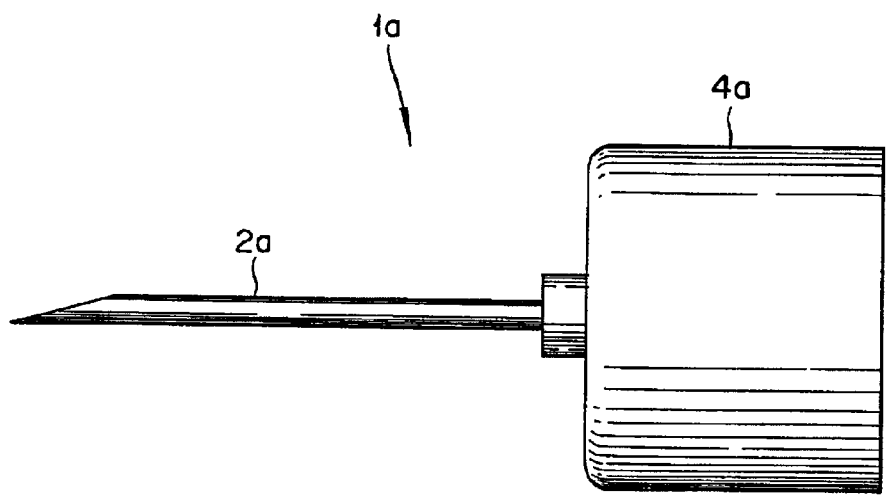
FIG. 10 is a side view of a drug injection needle according to a second embodiment of the invention.
Figure 11:
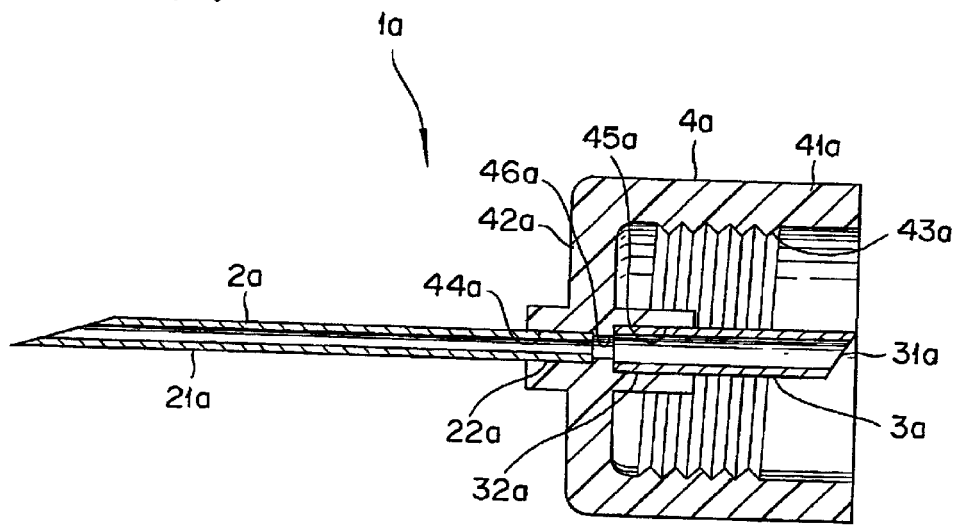
FIG. 11 is a cross sectional view of the drug injection needle show in FIG. 10.

FIG. 10 is a side view of a drug injection needle according to a second embodiment of the invention and FIG. 11 is a cross sectional view of the drug injection needle show in FIG. 10. In the following explanations, the areas that are different from the first embodiment will be explained primarily, skipping the descriptions the common parts.

The drug injection apparatus according to the second embodiment is different from the first embodiment only in the constitution of the drug injection needle, and the constitution of the injector main body 5 is the same.

As shown in FIG. 10 and FIG. 11, a drug injection needle 1a comprises a puncturing needle part 2a that has a puncturing part 21a that is capable of puncturing a living body, a drug introducing needle part 3a that is capable of communicating with the inside of the drug container 51, and a housing 4a that supports the puncturing needle part 2a and the drug introducing part 3a in such a way as to allow the liquid drug to flow between the needle parts 2a and 3a.

As shown in the drawings, the drug injection needle 1a according to the second embodiment is different in that the puncturing needle part 2a and the drug introducing needle part 3a constitute two separate needle bodies independently, from the drug injection needle 1 according to the first embodiment in which the puncturing needle part 2 and the drug introducing needle part 3 constitute a single needle body.

The housing 4a comprises a cylindrical part 41a and a bottom wall 42a formed on one end of the cylindrical part 41a. A female screw 43a is formed on the inner surface of the cylindrical part 41a to engage with the male screw 57 formed on the boss 53 of the drug container 51.

The puncturing needle part 2a constitutes a hollow needle, which is made of the same material as that of the puncturing needle part 2 of the above-described embodiment. The puncturing needle part 2a is affixed to the housing 4a with its root part 22a being inserted into an attaching hole 44a formed on the distal side of the bottom wall 42a of the housing 4a.

The drug introducing needle part 3a also constitutes a hollow needle, which is made of the same material as that of the drug introducing needle part 3 of the above-described embodiment. The drug introducing needle part 3a is affixed to a housing 4a with its root part 32a being inserted into an attaching hole 45a formed on the proximate end of the bottom wall 42a of the housing 4a. The drug introducing needle part 3a has a larger outer diameter than that of the puncturing part 21a of the puncturing needle part 2a.

A hole 46a connecting between the puncturing needle part 2a and the drug introducing part 3a is formed in the housing 4a.

The outer diameter of the drug introducing needle part 3a in the second embodiment should be preferably in the range of 0.3–2 mm, or more preferably in the range of 0.35–1.5 mm. Accordingly, the inner diameter of the drug introducing needle part 3a should be preferably in the range of 0.25–1.2 mm.

The affixing of the puncturing needle part 2a and the drug introducing needle part 3a to the housing 4a is conducted by insert molding or gluing, for example, in a shape as shown in FIG. 11. Since the puncturing needle part 2a and the drug introducing part 3a are formed of two separate needle bodies as shown in FIG. 11, the drug injection needle 1a can be manufactured by a conventional method without requiring any special method. Moreover, since the needle parts 2a and 3a are assembled to engage with the attaching holes 44a and 45a respectively, they are firmly affixed to the housing 4a.

Figure 12:
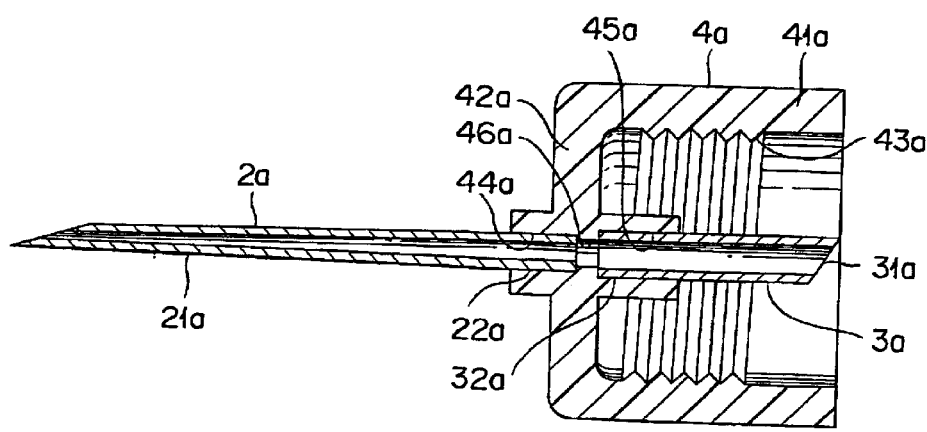
FIG. 12 is a cross sectional view of a variation of the drug injection needle according to the second embodiment of the invention.

If the drug injection needle 1a is a long needle normally used for subcutaneous and intramascular administration, it is not necessary to make the entire portion that can puncture a living body thinner than the drug introducing needle part 3a. For example, it is also possible to configure in such a way as to make the part with a continuously changing outer diameter to be able to puncture a living body as shown in FIG. 12, so that the part, which is on the proximate side having a constant and thick diameter, is affixed in the center of the bottom wall 42a of the housing 4a in an inserted condition. Furthermore, the shape extending from the puncturing part 21a to the part, which is affixed to the bottom wall 42a of the housing 4a, in this invention should not necessarily be limited to a shape having a constant outer diameter as shown in FIG. 11, but rather it can be a shape having a continuously changing outer diameter.

Figure 13:
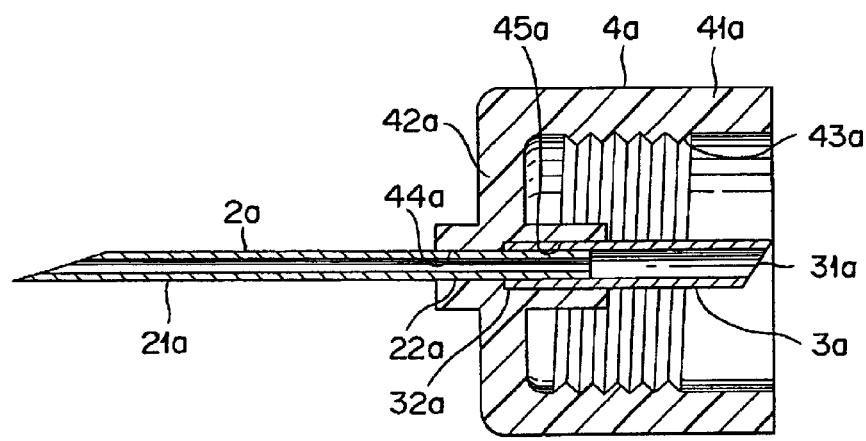
FIG. 13 is a cross sectional view of another variation of the drug injection needle according to the second embodiment of the invention.

Furthermore, the proximate end of the puncturing needle part 2a can be inserted into the opening of the distal end of the drug introducing needle part 3a so that the both needle parts 2a and 3a are affixed in advance in this invention as shown in FIG. 13. The affixing can be done by gluing and welding. The puncturing needle part 2a and the drug introducing needle part 3a affixed together in advance can be affixed to the housing 4a by means of insert molding or gluing in a shape as shown in FIG. 13.

Figure 14:
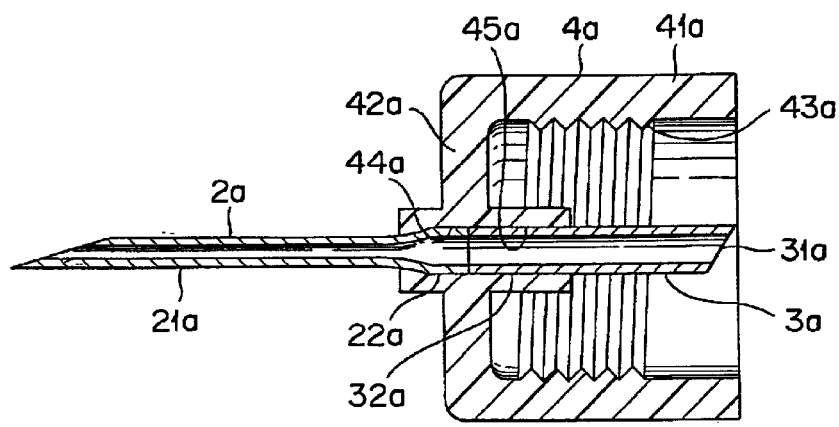
FIG. 14 is a cross sectional view of yet another variation of the drug injection needle according to the second embodiment of the invention.

Furthermore, the proximate end of the puncturing needle part 2a and the distal end of the drug introducing needle part 3a can be affixed together in advance as shown in FIG. 14. The affixing can be conducted by gluing or welding. In this case, it can be so arranged that the inner diameter in the vicinity of the junction between the puncturing needle part 2a and the drug introducing needle part 3a gradually reduce from the drug introducing needle part 3a to the puncturing part 21a of the puncturing needle part 2a (tapered shape). Consequently, the liquid drug is accelerated and flows vigorously as it flows from the drug introducing part 3a to the puncturing part 21a.

Furthermore, although each of the drug injection needles shown in FIG. 10 through FIG. 14 has only one puncturing needle part 2a, the drug injection needle of the invention is not limited to this arrangement, but rather it can be arranged to have multiple puncturing needle parts 2a corresponding to a single drug introducing needle part 3a. Moreover, multiple pairs of a puncturing needle part 2a and a drug introducing needle part 3a can be provided for a single housing 4a.

Figure 15:
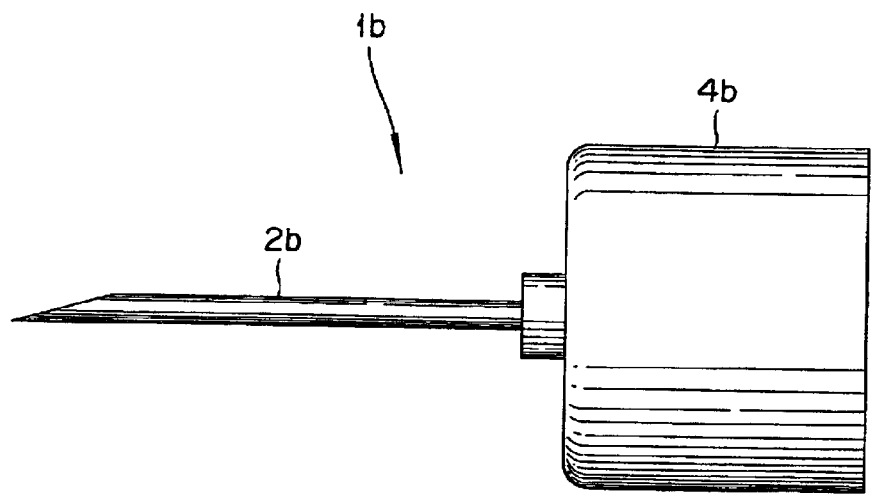
FIG. 15 is a side view of a drug injection needle according to a third embodiment of the invention.
Figure 16:
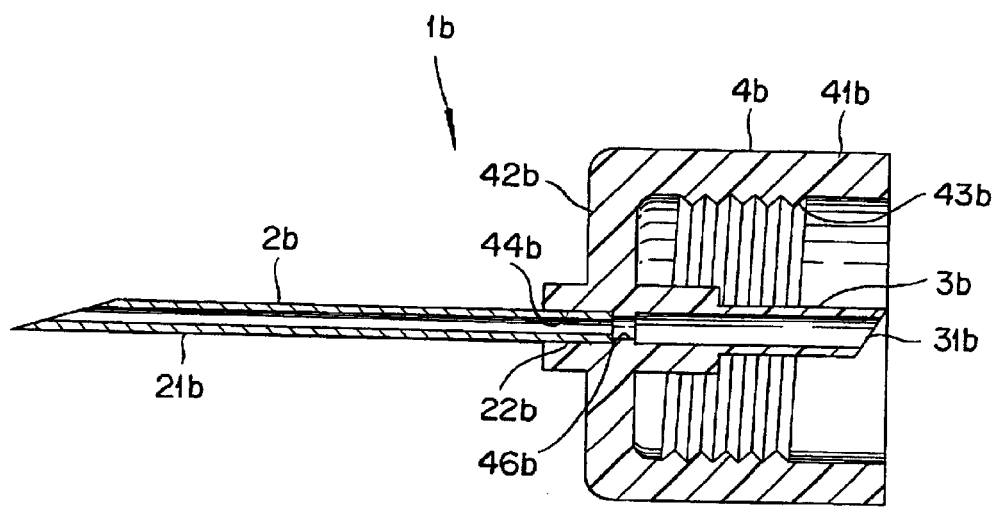
FIG. 16 is a cross sectional view of the drug injection needle show in FIG. 15.

FIG. 15 is a side view of a drug injection needle according to a third embodiment of the invention and FIG. 16 is a cross sectional view of the drug injection needle show in FIG. 15. In the following explanations, the areas that are different from the first embodiment will be explained primarily, skipping the descriptions of common parts.

The drug injection apparatus according to the third embodiment is different from the first embodiment only in the constitution of the drug injection needle, and the constitution of the injector main body 5 is the same.

As shown in FIG. 15 and FIG. 16, a drug injection needle 1b comprises a puncturing needle part 2b that has a puncturing part 21b that is capable of puncturing a living body, a drug introducing needle part 3b that is capable of communicating with the inside of the drug container 51, and a housing 4b that supports the puncturing needle part 2b and the drug introducing needle part 3b in such a way as to allow the liquid drug to flow between the needle parts 2b and 3b.

As shown in the drawings, the drug injection needle 1b according to the third embodiment is different in that the drug introducing needle part 3b and the housing 4b are formed integrally with the same material, from the drug injection needle 1 according to the first embodiment, in which the puncturing needle part 2 and the drug introducing needle part 3 constitute a single needle body, or from the drug injection needle 1a according to the second embodiment, in which the puncturing needle part 2a and the drug introducing needle part 3a constitute two separate needle bodies independently.

The housing 4b comprises a cylindrical part 41b and a bottom wall 42b formed on one end of the cylindrical part 41b. A female screw 43b is formed on the inner surface of the cylindrical part 41b to engage with the male screw 57 formed on the boss 53 of the drug container 51.

The puncturing needle part 2b constitutes a hollow needle which is made of the same material as that of the puncturing needle parts 2 and 2a of the above-described embodiments. The puncturing needle part 2b is affixed to the housing 4b with its root part 22b being inserted into an attaching hole 44b formed on the distal side of the bottom wall 42b of the housing 4b.

The drug introducing needle part 3b is formed on the proximate side of the bottom wall 42b when it is formed integrally with the housing 4b from the same material. The material used for the drug introducing needle part 3b and the housing 4b is the same material used for the housings 4 and 4a of the above-described embodiments. The cutting edge 31b is formed on the proximate end of the drug introducing needle part 3b in order to penetrate through the elastic member 55 that seals the drug injection port 54 formed on the distal end of the drug container 51. The cutting edge 31b is, for example, formed simultaneously with the molding process of the drug introducing needle part 3b and the housing 4b. The cutting edge 31b can also be formed by slicing the end of the drug introducing needle part 3a in an angle. The shape of the cutting edge 31b can have any shape as long as it is suitable to penetrate through the elastic member 55; for example, it can be a conically pointed shape. The drug introducing needle part 3b has a larger outer diameter than that of the puncturing part 21b of the puncturing needle part 2b.

A hole 46b is formed on the housing 4b for connecting between the puncturing needle part 2b and the drug introducing needle part 3b.

The outer diameter of the drug introducing needle part 3b in the third embodiment should be preferably in the range of 0.3–2 mm, or more preferably in the range of 0.35–1.5 mm. Accordingly, the inner diameter of the drug introducing needle part 3b should be preferably in the range of 0.25–1.2 mm.

The affixing of the puncturing needle part 2b to the housing 4b is conducted by insert molding or gluing, for example, in a shape as shown in FIG. 16. Since the drug introducing part 3b is formed integrally with the housing 4b from the same material as shown in FIG. 16, the drug injection needle 1b can be manufactured by a conventional method without requiring any special method. Moreover, since the puncturing needle part 2b is assembled to engage with the attaching hole 44b, it is firmly affixed to the housing 4b.

If the drug injection needle 1b is a long needle normally used for subcutaneous and intramascular administration, it is not necessary to make the entire portion that can puncture a living body thinner than the drug introducing needle part 3b.

Figure 17:
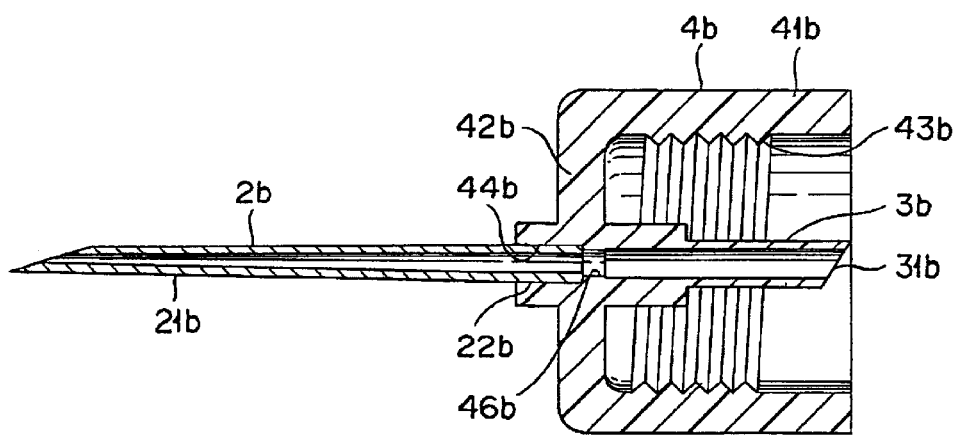
FIG. 17 is a cross sectional view of a variation of the drug injection needle according to the third embodiment of the invention.

For example, it is also possible to configure in such a way as to make the part with a continuously changing outer diameter to be able to puncture a living body as shown in FIG. 17, so that the part, which is on the proximate side having a constant and thick diameter, is affixed in the center of the bottom wall 42b of the housing 4b in an inserted condition. Furthermore, the shape extending from the puncturing part 21b to the part, which is affixed to the bottom wall 42b of the housing 4b, in this invention should not necessarily be limited to a shape having a constant outer diameter as shown in FIG. 16, but rather it can be a shape having a continuously changing diameter.

Figure 18:
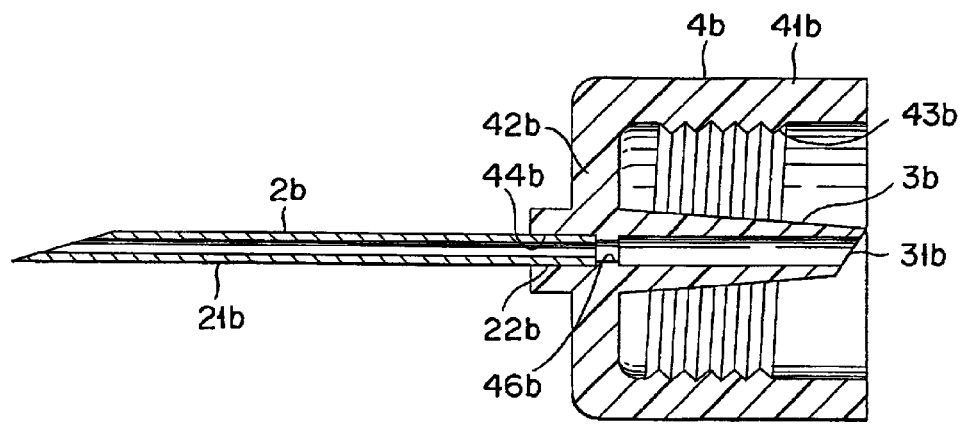
FIG. 18 is a cross sectional view of another variation of the drug injection needle according to the third embodiment of the invention.

Furthermore, it is also possible to make only the outer diameter reduce gradually toward the cutting edge 31b (tapered shape) while maintaining the inner diameter of the drug introducing needle part 3b constant as shown in FIG. 18. This makes it easier to cause the drug introducing needle part 3b to penetrate the elastic member 55 that seals the drug injection port 54 formed at the distal end of the drug container 51.

Figure 19:
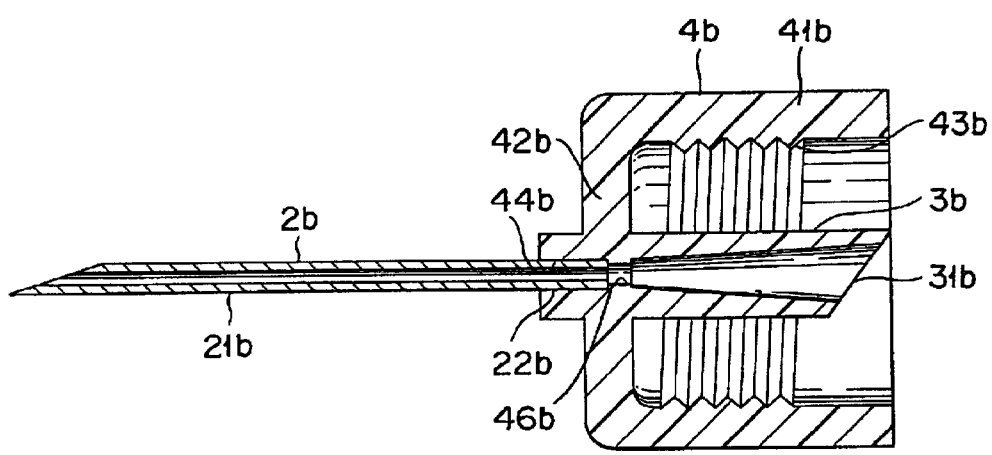
FIG. 19 is a cross sectional view of yet another variation of the drug injection needle according to the third embodiment of the invention.

Furthermore, it is also possible to make only the inner diameter increase gradually toward the cutting edge 31b (tapered shape) while maintaining the outer diameter of the drug introducing needle part 3b constant as shown in FIG. 19. Consequently, the liquid drug is accelerated and flows vigorously as it flows from the drug introducing part 3b to the puncturing part 21b.

Furthermore, it is of course possible to make the outer diameter reduce gradually toward the cutting edge 31b (tapered shape) while gradually increasing the inner diameter toward the cutting edge 31b (tapered shape).

Furthermore, although each of the drug injection needles shown in FIG. 15 through FIG. 19 has only one puncturing needle part 2b, the drug injection needle of the invention is not limited to this arrangement, but rather it can be arranged to have multiple puncturing needle parts 2b corresponding to a single drug introducing needle part 3b. Moreover, multiple pairs of a puncturing needle part 2b and a drug introducing needle part 3b can be provided for a single housing 4b.

It is obvious that this invention is not limited to the particular embodiments shown and described above but may be variously changed and modified without departing from the technical concept of this invention.

This application is based on Japanese Patent Application Nos. 2000-280631 filed on Sep. 14, 2000 and 2000-389248 filed on Dec. 21, 2000, the contents of which are hereby incorporated by reference.

What is claimed is:

1. An injection needle to be attached to a liquid injection port formed on the distal end of a liquid container that contains insulin solution or dental drug inside, comprising:

a puncturing needle part having a puncturing part capable of puncturing a body;

a liquid introducing needle part capable of communicating with the inside of said liquid container, said puncturing needle part and said liquid introducing needle part constituting a single needle body, said puncturing needle part having an intermediate part formed between said puncturing part and said liquid introducing needle part and connecting them smoothly by changing its diameter continuously;

the puncturing needle part and the liquid introducing needle part being made of metallic material, and a central axis extending from a proximal end of the liquid introducing needle cart to a distal end of the puncturing needle part being straight; and a housing that supports said puncturing needle part and said liquid introducing needle part in such a way as to allow the liquid to flow between the two needle parts, the housing including a bottom wall wherein;

at least a portion of said puncturing part having a constant outer diameter in the range of 0.15 mm–0.22 mm, the length of the portion of constant outer diameter being in the range of 0.2 mm–8 mm;

said puncturing part has an inner diameter in the range of 0.05 mm–0.15 mm;

said intermediate part having a shape tapering thinner toward the distal end and an inner diameter gradually reducing toward the distal end;

said puncturing needle part has a length extending from the bottom wall of the housing that is in a range 0.5 mm–10 mm;

said liquid introducing needle part has a larger outer diameter than at least the vicinity of the distal end of said puncturing part;

said liquid introducing needle part having an inner diameter in the range of 0.25 mm-0.5 mm and an outer diameter in the range of 0.3 mm–0.6 mm; and a cutting edge is formed at the end of said liquid introducing needle part for penetrating through an elastic member that is provided to seal the liquid injection port.

2. An injection needle of claim 1, wherein the outer diameter of said puncturing part is in the range of 0.18–0.22 mm.

3. An injection needle of claim 1, wherein said liquid contains a drug that acts on the living body.

4. An injection needle according to claim 1, wherein the housing includes an inner surface provided with a screw thread that is adapted to threadably engage an external screw thread on the liquid injection port.

5. An injection apparatus including a liquid container that contains liquid inside and has a liquid injection port formed on its distal end and an elastic member provided to seal the liquid injection port, and an injection needle that is attached to the liquid injection port of said liquid container, wherein:

said injection needle comprises a puncturing needle part having a puncturing part capable of puncturing a body, a liquid introducing needle part capable of communicating with the inside of said liquid container; and a housing that supports said puncturing needle part and said liquid introducing needle part in such a way as to allow the liquid flow between the two needle parts;

the puncturing needle part and the liquid introducing needle part being made of metallic material, and a central axis extending from a proximal end of the liquid introducing needle part to a distal end of the puncturing needle part being straight;

said puncturing needle part and said liquid introducing needle part constitute a single needle body, said puncturing needle part having an intermediate part formed between said puncturing part and said liquid introducing needle part and connecting them smoothly by changing its diameter continuously;

at least a portion of said puncturing part having a constant outer diameter in the range of 0.15mm–0.22 mm, the length of the portion of constant outer diameter being in the range of 0.2 mm–8 mm;

said puncturing part has an inner diameter in the range of 0.05 mm–0.15 mm;

said puncturing needle part has a length extending from a bottom wall of the housing that is in a range 0.5 mm–10 mm;

said intermediate part having a shape tapering thinner toward the distal end and an inner diameter gradually reducing toward the distal end;

said liquid introducing part has a larger outer diameter than at least the distal end of said puncturing part;

said liquid introducing needle part having an inner diameter in the range of 0.25 mm-0.5 mm and an outer diameter in the range of 0.3 mm–0.6 mm; and a cutting edge is formed at an end of said liquid introducing needle part for penetrating through said elastic member.

6. An injection apparatus according to claim 5, wherein the housing includes an inner surface provided with a screw thread that threadably engages an external screw thread on the liquid injection port.

* * * * *